United States Patent
Öhman et al.

(12)

(10) Patent No.: US 6,210,966 B1
(45) Date of Patent: Apr. 3, 2001

(54) CULTURE MEDIUM FOR INSECT CELLS LACKING GLUTAMINE AN CONTAINS AMMONIUM SALT

(75) Inventors: Lars Öhman, Stockhom; Lena Häggström, Sollentuna, both of (SE)

(73) Assignee: Karo Bio AB, Huddinge (SE)

(*) Notice: Subject to any disclaimer, the term of this patent is extended or adjusted under 35 U.S.C. 154(b) by 0 days.

(21) Appl. No.: 08/913,981

(22) PCT Filed: Mar. 21, 1996

(86) PCT No.: PCT/EP96/01281
§ 371 Date: Dec. 8, 1997
§ 102(e) Date: Dec. 8, 1997

(87) PCT Pub. No.: WO96/30500
PCT Pub. Date: Oct. 3, 1997

(30) Foreign Application Priority Data

Mar. 27, 1995 (GB) .................................................. 9506249

(51) Int. Cl.[7] .............................. C12N 5/00; C12N 5/02; C12N 5/06; C12N 5/10
(52) U.S. Cl. ............................................. 435/348; 435/404
(58) Field of Search ...................................... 435/348, 404

(56) References Cited

FOREIGN PATENT DOCUMENTS

2205572 * 5/1974 (FR) .

OTHER PUBLICATIONS

Suzuki et al., Elucidation of Amidating Rxn Mech. by Frog amidating enzyme . . . Expressed in Insect Culture, EMBO, see abstract, 1990.*

Invertebrate Cell Culture Applications, 1982, Academic Press, Inc., New York; pp. 9 & 38.*

Biotechnology and Bioengineering Including: Symposium Biotechnology In Energy Production and Conservation., vol. 42, No. 6, May 9, 1993, New York, US., see pp. 697–707.*

Ohman et al., "Induction of a Metabolic Switch in Insect Cells by Substrate–Limited Fed Batch Cultures", Appl Microbial Biotechnol. 73:1006–1013, pp. 1006–1013, 1995.*

* cited by examiner

*Primary Examiner*—David M. Naff
*Assistant Examiner*—Deborah K. Ware
(74) *Attorney, Agent, or Firm*—Todd E. Garabedian; Wiggin & Dana

(57) ABSTRACT

A culture medium for growth of insect cells, such as *Spodoptera frugiperda*, is provided. The culture medium lacks glutamine, and may optionally lack glutamate and/or aspartate. Further the insect culture medium contains an ammonium ion source, such as an ammonium salt. The culture medium is particularly useful for culturing the insect cells for a variety of purposes, for example, producing proteins or polypeptides using a baculovirus expression system.

9 Claims, 4 Drawing Sheets

CULTURE MEDIUM FOR INSECT CELLS LACKING GLUTAMINE AN CONTAINS AMMONIUM SALT

BACKGROUND OF THE INVENTION

1. Field of the Invention

This application concerns a culture medium for insect cells.

2. Brief Description of the Art

The baculovirus expression system using insect cells has become an important tool for production of recombinant proteins for several reasons. First, the expression levels are often very high compared to those obtained in other animal cells, such as CHO-cells. Second, proteins produced using this system are often biologically active due to the insect cells' ability to perform post-translational modifications, folding and assembly of most proteins. Third, the time from cloning to production of the protein is short compared to the time needed to construct a stably transformed animal cell line. Fourth, cell death inevitably follows virus infection of insect cells. This can be an advantage over other expression systems because it may permit better expression of cytotoxic, regulatory or essential cellular genes.

Foreign proteins are produced during a lytic infection of insect cells with a recombinant virus. Baculoviruses contain a very late hyper-expressed gene, polyhedrin, which is not essential for viral replication. Placing a gene under control of the polyhedrin promoter allows the production of large quantities of a recombinant protein. The strategy for production of a protein involves three distinct stages:

(a) growing the insect cells from mid to late growth phase;
(b) infecting the cells with virus containing a gene encoding the protein of interest; and
(c) harvesting and purification of the protein product.

Insect cells are conventionally cultured in complex media containing inorganic salts and sometimes organic salts, amino acids, sugars, vitamins, trace elements, lipids and protein hydrolysates. For example one commercially available medium, called, IPL-41, is available from a number of suppliers. Apart from these components, serum or yeast extract has conventionally been added to provide undefined but essential nutrients. The amino acid glutamine has hitherto been assumed to be essential for cultured insect cells (Wang, M-Y et al Biotechnol. Prog. 1993, 9, 355–361; Kamen, A. A. et al Biotechnol. Bioeng. 1991, 38, 619–628;Wang, M-Y et al Biotechnol. Prog. 1993 in press), as it is for most cultured mammalian cell lines.

BRIEF SUMMARY OF THE INVENTION

We have surprisingly found that insect cells are capable of synthesising glutamine themselves. The ability of insect cells to grow without an external glutamine source has not been described in the literature before. We have now shown that insect cells are, indeed, able to grow without glutamine supplied to the medium and that insect cells are, in fact, capable of growing in a medium without glutamine, glutamate or aspartate.

According to one aspect of the invention there is provided a medium, for example for culturing insect cells for producing proteins or polypeptides using a baculovirus expression system, characterized in that the medium does not contain glutamine.

The medium may also optionally not contain glutamate and/or aspartate.

The medium of the invention can be used for growth of the cells for the production of recombinant proteins.

The medium of the invention has several advantages over traditional, glutamine-containing, insect cell culture media. First, glutamine is generally considered problematic in cell culture because of its instability. It decomposes spontaneously to pyrrolidone carboxylic acid and ammonia in aqueous solution. This instability is the major factor limiting the storage life of a cell culture medium. A medium without glutamine thus results in a markedly longer storage life. The medium of the invention is also less expensive and simpler to prepare. Further, cells growing in the medium of the invention exhibit a more efficient metabolism and a decreased secretion of by-products that may be inhibitory to growth.

Preferably, the medium comprises an ammonium salt or another ammonium ion source or at least one amino acid or another compound that can be converted to ammonium ions. An external ammonium ion source is then used as a nitrogen source for biosynthesis of amino acids. Preferably, the concentration of ammonium in the medium is up to 20 mM. However, during certain conditions, as for example, in substrate limited cultures, the cells may liberate ammonium themselves which in turn can be used for biosynthesis. Under these conditions addition of ammonium is not necessary for growth.

According to another aspect of the invention, there is provided a method of culturing insect cells, the method comprising growing the cells in a medium according to the invention.

According to a further aspect of the invention we provide a method of obtaining a polypeptide including transforming insect cells with recombinant baculovirus including a gene coding for said polypeptide, and growing the transferred cells in a culture medium that does not contain glutamine but which does contain an ammonium ion source.

The insect cells may for example be from the fall armyworm, *Spodoptera frugiperda*.

BRIEF DESCRIPTION OF THE DRAWINGS

The preparation and use of a medium in accordance with the invention will now be described, by way of example only, with reference to the accompanying drawings FIGS. 1 to 5 in which.

DETAILED DESCRIPTION OF THE INVENTION

EXAMPLE 1

Figure 1:
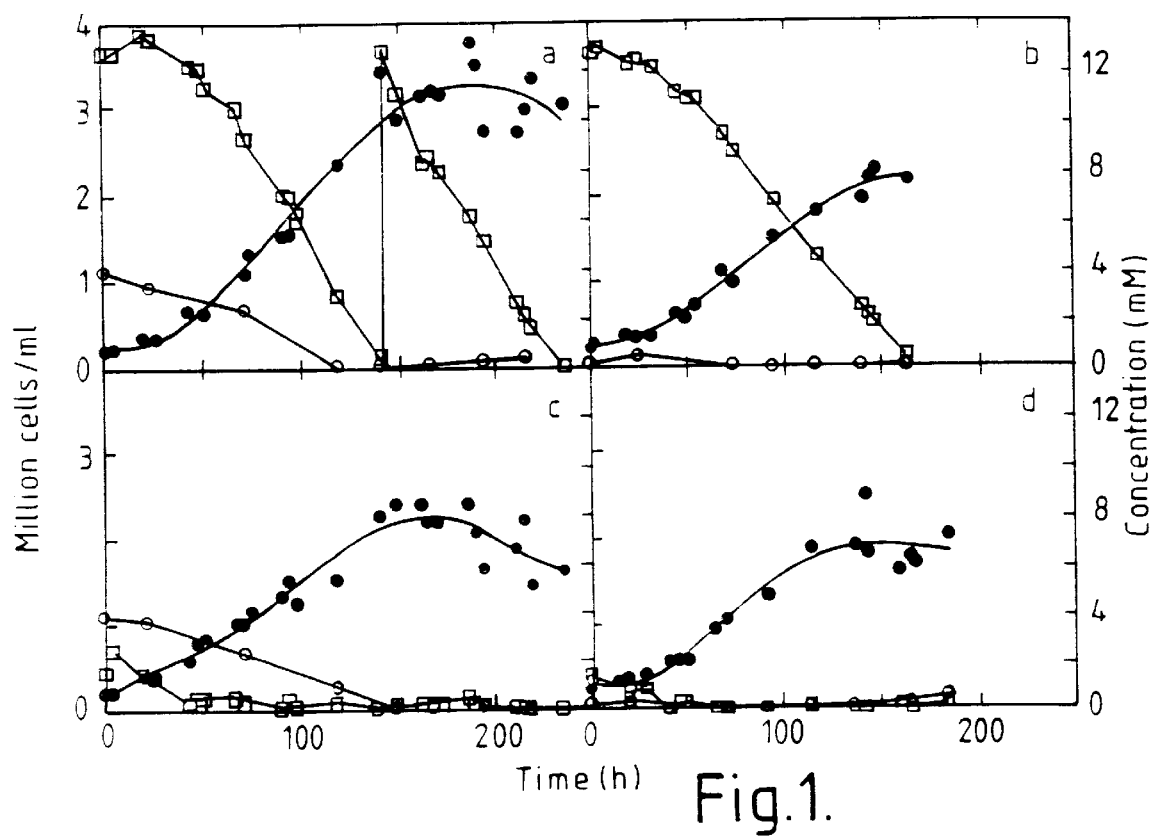
FIG. 1 illustrates the growth of insect cells in different media.

*Spodoptera frugiperda* (Sf-9) cells were cultivated in suspension culture in spinner flasks (Techne, 125 ml) with 50 ml medium, stirred at 60 rpm and incubated at 27° C. A new culture was started every second month from ampoules stored in liquid nitrogen. The basic medium used (KBM502) had the following composition in $gl^{-1}$: glucose, 2.5; KCl, 2.87; $CaCl_2$, 1.0: $MgCl_2$, 1.07; $MgSO_4$, 1.36; $NaHCO_3$, 0.35; $NaH_2PO_4$, 0.88; choline chloride, 0.02; glutamine 1.0; L-arginine-HCl, 7.0; L-asparagine, 3.5; L-aspartic acid, 3.5; L-glutamic acid, 6.0; L-glycine, 6.5; L-histidine-HCl, 2.0; L-isoleucine, 0.5; L-leucine, 0.75; L-lysine-HCl, 6.25; L-methionine, 0.5; L-phenylalanine, 1.5; L-proline, 3.5; L-serine, 5.5; L-threonine, 1.75; L-valine, 1.0; L-cystine-2 HCl, 0.5; L-tryptophan, 1.0; L-tyrosine, 0.72; and, in $\mu gl^{-1}$; para-amino benzoic acid, 320; biotin, 160; D-calcium pantothenate, 80; folic acid, 80; myo-inositol, 400; niacin, 160; pyridoxine-HCl, 400; riboflavin, 80; thiamine-HCl, 80; vitamin B-12, 240; $COCl_2.6\ H2O$, 50; $FeSO_4.7H_2O$, 550; $MnCl_2O$, 20; $(NH_4)_6.(Mo_7O_{24}4H_2O)$, 40; $CuCl_2$, 158; and $ZnCl_2$, 40. The medium was supplemented with 10% FCS (Gibco), and 50 mg 1-1 Gentamicin (Sigma). In the bioreactor experiments, 0.1% Pluronic F-68 (Sigma), 40 ppm Anti foam C (Sigma) was added to the medium.

Glutamine, glutamate and aspartate were omitted from the medium as indicated below. The concentration of $NH_4Cl$ (when added) was 5 mM.

Spinner Flask Cultures

In the first experiment three media were tested a) KBM502 without glutamine, b) KBM502 with 5 mM $NH_4Cl$ but without glutamine, and c) KBM502 with 1 $gl^{-1}$ glutamine (control culture).

In the second experiment the following media were tested a) KBM502 with 5 mM $NH_4Cl$, without glutamine, b) KBM502 with 5 mM $NH_4Cl$, without glutamine or glutamate, c) KBM502 with 5 mM $NH_4Cl$, without glutamine, glutamate or aspartate.

Each medium was tested for growth of cells in triplicate. Spinner flasks containing 50 ml of medium were inoculated to a cell density of $2.5 \times 10^5$ cells/$ml^{-1}$. The cells were counted once a day.

Bioreactor Cultures

The medium used for bioreactor cultures was essentially the same as KBM502, but with the following modifications: it contained Tryptose Broth (Sigma) 2.6 $gl^{-1}$; the amino acid composition was slightly different (1×Grace's amino acid solution modified for TC 100 (Sigma)) and the normal concentration of glutamine was 0.6 $gl^{-1}$.

Tank reactors with a working volume of 3.0 (Belach Bioteknik AB, Stockholm, Sweden) equipped with one three blade marine impeller (d=70 mm) were used. The stirring speed was 100 rpm and DOT was controlled at 30% by intermittent sparging of oxygen at 200 ml $min^{-1}$. Air was also passed above the surface at 100 ml $min^{-1}$. The pH of the medium was initially 6.2 but was not controlled during culture. The culture temperature was maintained at 27° C. Inoculua were prepared from spinner flask cultures. The cells were centrifuged and resuspended in fresh medium prior to inoculation. The initial cell density in the bioreactor was $2 \times 10^5$ cells $ml^{-1}$.

In batch cultures the medium was supplemented with 2.5 g $l^{-1}$ glucose and 0.6 $gl^{-1}$ glutamine. In the glucose fed-batch culture a glucose solution (15 $gl^{-1}$) was continuously pumped into the reactor(1.8 ml $h^{-1}$) from the time of exhaustion (42 h) of the amount of glucose supplied by the tryptose broth; and 0.6 $gl^{-1}$ of glutamine was supplemented from the beginning of the culture. In the glutamine-limited culture no glutamine was present in the initial medium but was fed (1.8 ml $h^{-1}$) into the bioreactor using a glutamine solution (3 $gl^{-1}$) from the beginning of the experiment. Glucose (2.5 $gl^{-1}$) was added from the beginning. The combined glucose and glutamine fed-batch culture was fed initially with only a glutamine solution but when the initial amount of glucose was exhausted (44.5 h), a mixed solution of glucose (15 $gl^{-1}$) and glutamine (3 $gl^{-1}$) was fed at a rate of 1.8 ml $h^{-1}$.

Sampling and Analyses

Cell counting was performed using a Buker counting chamber and cell viability was determined by trypan blue exclusion. Samples for ammonium, lactate, glucose, amino acid and other organic acid determinations were centrifuged and stored frozen until analyzed. The ammonium ion concentration was measured with an ammonium selective electrode (Orion). Lactate and uric acid were analyzed enzymatically using test kits from Sigma while citrate and succinate were determined by test kits from Boehringer Mannheim. Glucose was analyzed with an YSl glucose analyzer. Analyses of amino acids were performed on a Biotronik LC 5001 amino acid analyzer using ninhydrin as detection reagent.

Batch and Fed Bath Bioreactor Cultures

The growth of Sf-9 cells and the concentration of glucose and glutamine in a) a batch; b) a glutamine-limited fed batch c) a glucose-limited fed batch; and d) a dual glucose and glutamine-limited fed batch culture is shown in FIG. 1. Symbols: viable cells, filled squares; glucose, open squares; glutamine, open circles.

Figure 2:
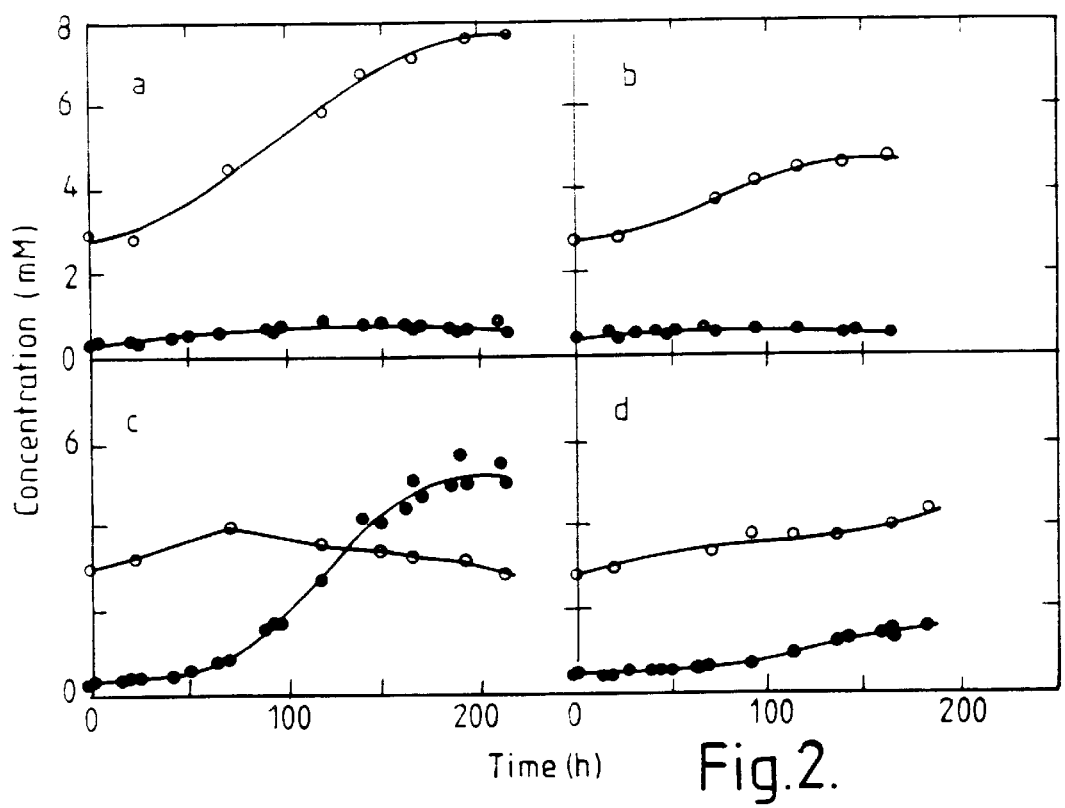
FIG. 2 illustrates the production of alanine and ammonium ions by insect cells under different conditions.

FIG. 2 illustrates the production of alanine and ammonium ions by Sf-9 cells in a) batch culture, b) glutamine-limited fed batch culture, c) glucose-limited fed batch culture, and d) dual glucose- and glutamine-limited fed batch culture. Symbols: Alanine -O- and ammonium -●- formation by Sf-9 cells.

In the batch culture the formation of alanine was considerable—a typical metabolic response of insect cell cultures (FIG. 2a). The concentration of alanine increased from 3 mM at the start to almost 8 mM. On the contrary, the formation of ammonium ions was insignificant.

In the glucose-limited fed batch culture, the glucose feeding was started at 42 h when the initial quantity of glucose, (unfortunately supplied by the tryptose broth) was consumed (FIG. 1c). After that the glucose concentration remained very low (below 0.2 mM) throughout the culture. The formation of alanine is not only completely depressed, but alanine is actually consumed after glucose limitation was established, while, at the same time, ammonium production is triggered (FIG. 2c). The concentration of ammonium ions increases abruptly from 0.5 mM to around 4 mM. Ammonium formation continues, although at a lower rate, after depletion of glutamine (150 h), indicating that it is released also from other amino acids.

In the glutamine-limited culture, glutamine was fed at a constant rate from the beginning resulting in a small increase in concentration to a maximum of 0.5 mM whereafter it declined below the detection limit (FIG. 1b). In this type of culture alanine production takes place (FIG. 2b) but the accumulation is less than that in the batch culture. No increase in ammonium ion concentration is observed.

Finally, in the glucose and glutamine-limited culture, where glutamine and glucose were fed simultaneously, low concentrations of both substrates were established (FIG. 1d). Very little alanine or ammonium was formed in this culture (FIG. 2d).

During glutamine limitation, the consumption of glutamine was much less than that of any other amino acid as shown in the Table.

This small amount seemed insufficient for the biosynthetic need of the cells. Therefore it would appear that glutamine biosynthesis occurs in the glutamine-limited cultures. The increase in the concentration of glutamine in the stationary phase of the batch culture, after exhaustion of the initial amount (FIG. 1a), also supports the idea that Sf-9 cells can synthesise glutamine. From the Table it is also evident that the consumption of glutamate and aspartate increased in the fed batch cultures.

Growth of Insect Cells in Medium without Glutamine

Figure 3:
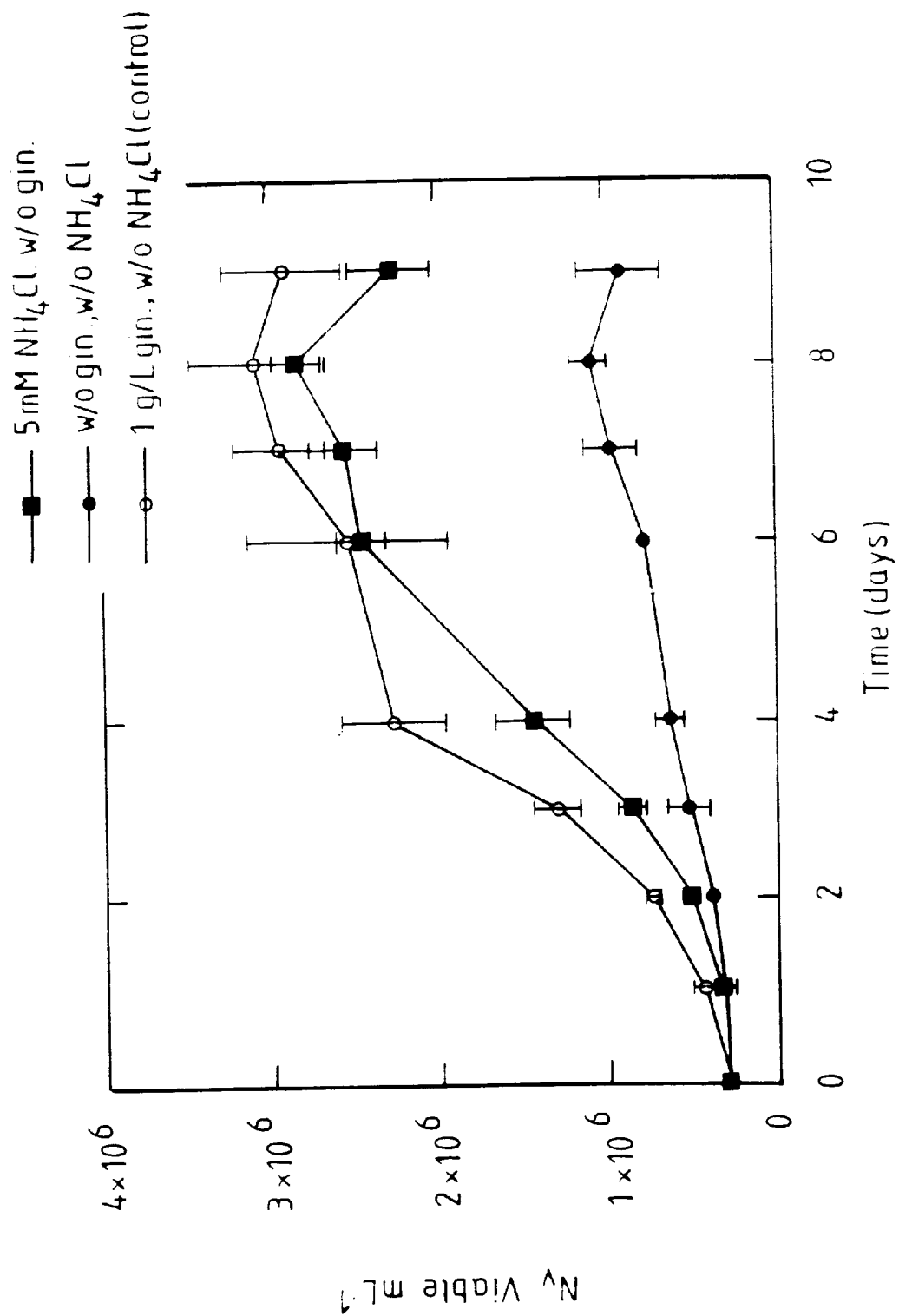
FIG. 3 illustrates the growth of insect cells under different conditions.

FIG. 3 illustrates the growth of cells cultivated in media with or without glutamine and with or without 5 mM $NH_4Cl$ Cells cultivated in a medium without glutamine but supplemented with $NH_4Cl$, reached almost the same maximum cell density, $2.9 \times 10^6$ cells $ml^{-1}$, as cells cultivated in a standard medium containing glutamine, although the growth rate is somewhat lower (FIG. 3). This may be explained by the extra burden that the synthesis of glutamine exerts on the cells. Cells grown in a medium lacking both glutamine and $NH_4Cl$ grow very poorly; the maximum cell density does not exceed $6 \times 10^4$ cells/ml (FIG. 3). This experiment has been repeated many times, and the cell culture has now been maintained in a medium lacking glutamine for several months.

This experiment clearly demonstrates that Sf-9 cells are capable of growing well without an external source of glutamine, provided that ammonium ions are supplied to the medium. To add an ammonium salt to a medium for animal cells has generally been regarded as very unfavourable, as external ammonium is inhibitory for most cultured animal cells, even at rather low levels. We cannot see any negative effects of added $NH_4Cl$ below a concentration of 20 mM.

Biosynthesis of glutamine, by glutamine synthetase, requires the substrates glutamate and ammonium. We have shown earlier that no ammonium was formed during growth of Sf-9 cells in a batch culture with excess glucose (FIG. 2a) and in a glutamine limited culture with excess glucose (FIG. 2b). Thus, external ammonium has to be supplied as a nitrogen source for the biosynthesis of glutamine. However, during glucose limitation Sf-9 cells excreted ammonium into the medium (FIG. 2c). In such and similar cases it may not be necessary to add ammonium to the medium.

Growth of Insect Cells in Medium without Glutamine, Glutamate and Aspartate

Figure 4:
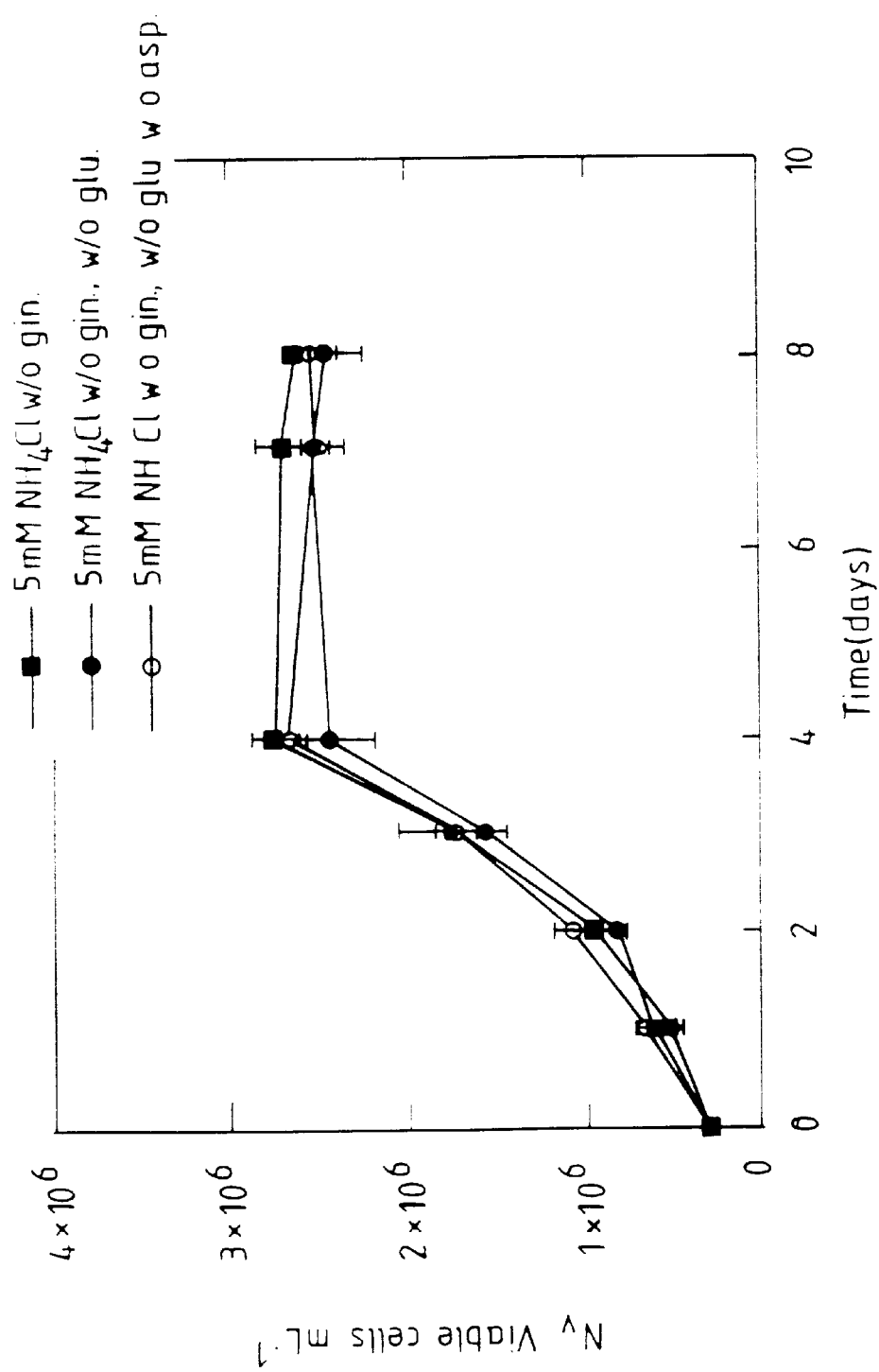
FIG. 4 illustrates the growth of insect cells in different media.

FIG. 4 illustrates the growth of insect cells in medium without glutamine, glutamate and aspartate. FIG. 4 clearly shows that Sf-9 cells are able to grow without external sources of glutamine, glutamate, glutamate and aspartate, provided that ammonium is supplied to the medium. No significant difference can be seen in the growth between the three media.

These results indicate further that Sf-9 cells do indeed synthesize glutamine, glutamate and aspartate because all three amino acids are needed for various biosynthetic functions and for protein synthesis. It is likely that glucose and ammonium ions are the ultimate substrates for the synthesis of the three amino acids. In this respect, the metabolism of Sf-9 cells resembles that of many microorganisms, but it is a very uncommon type of metabolism in cultured animal cells.

Further experimentation has confirmed that Sf-21 cells are capable of growing in a medium containing no glutamine but to which 5 mM $NH_4Cl$ has been added.

EXAMPLE 2

Expression of β-galactosidase in a Glutamine-free Medium

Figure 5:
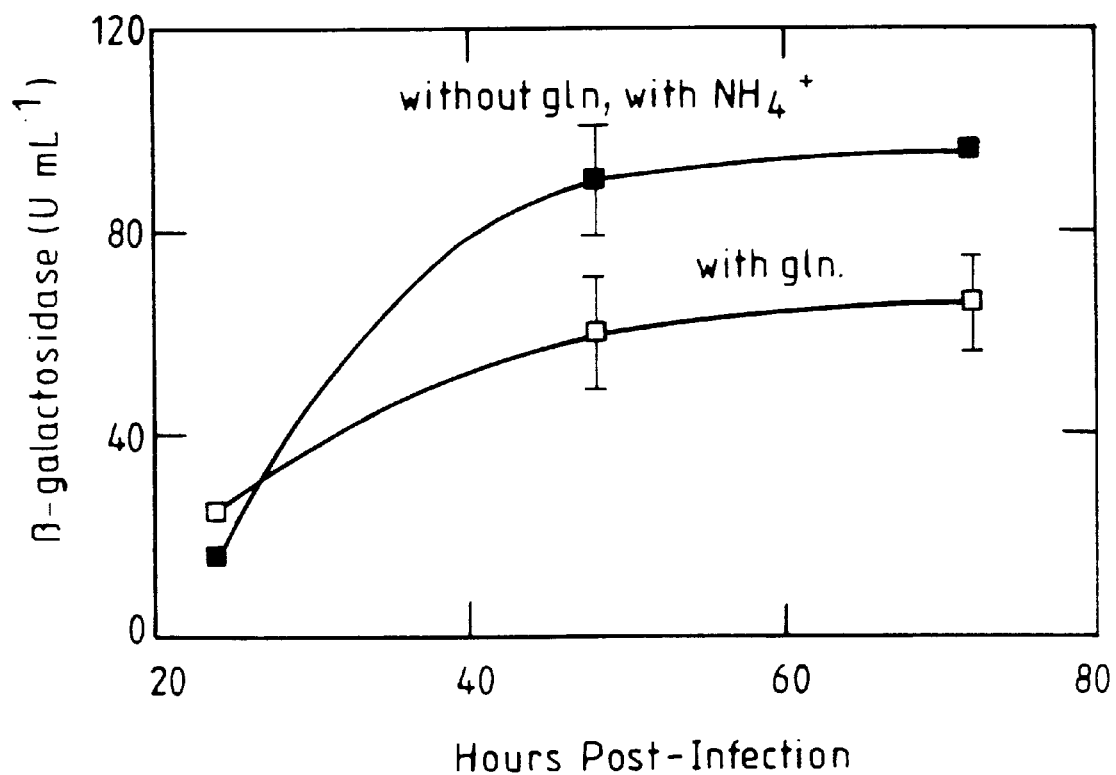
FIG. 5 illustrates the expression of the β-galactosidase gene from cells grown in a medium according to the invention.

To study the effect of glutamine-free conditions on recombinant protein production, Sf-9 cells were infected with a recombinant baculovirus during growth in the glutamine-free but ammonium supplemented medium (5 mM $NH_4Cl$) and the result compared to that from standard conditions (i.e. a medium with glutamine but without added $NH_4Cl$). The yield of β-galactosidase (24–72 h after infection, FIG. 5) indicates that the production of the recombinant protein is not negatively affected by the glutamine-free conditions.

TABLE

Consumption of amino acids in batch and fed batch (FB) cultures of insect cells.

| | Consumption ($\mu mol/10^6$ cells)[1] | | | |
|---|---|---|---|---|
| Amino acid | Batch | Glucose Fed Batch | Glutamine Fed Batch | Glucose and Glutamine Fed Batch |
| Glutamine | 1.85 | 1.85 | 0.04 | 0.02 |
| Glutamate | 0.11 | 0.29 | 0.45 | 0.62 |
| Aspartate | 0.01 | 0.03 | 0.34 | 0.20 |
| Asparagine | 0.09 | 0.15 | 0.28 | 0.26 |
| Serine | 0.46 | 0.33 | 0.76 | 0.70 |
| Lysine | 0.13 | 0.22 | 0.37 | 0.40 |
| Threonine | 0.11 | 0.13 | 0.21 | 0.21 |
| Arginine | 0.23 | 0.27 | 0.40 | 0.43 |
| Valine | 0.14 | 0.11 | 0.20 | 0.27 |
| Isoleucine | 0.16 | 0.10 | 0.17 | 0.20 |
| Leucine | 0.29 | 0.25 | 0.36 | 0.36 |
| Tyrosine | 0.12 | 0.10 | 0.16 | 0.12 |
| Phenylalanine | 0.12 | 0.10 | 0.15 | 0.17 |
| Tryptophan | 0.04 | 0.07 | 0.08 | 0.07 |
| Methionine | 0.15 | 0.15 | 0.18 | 0.15 |

[1]Calculated from the beginning of the culture up to the formation of two million cells/ml.

What is claimed is:

1. An insect cell culture medium for culturing *Spodoptera frugiperda*, wherein the insect cell culture medium does not contain glutamine and contains an added ammonium salt.

2. The insect cell culture medium of claim 1, wherein the insect culture medium further does not contain glutamate.

3. The insect cell culture medium of claim 2, wherein the insect culture medium further does not contain aspartate.

4. A method of culturing *Spodoptera frugiperda* insect cells, comprising the steps of:

growing the *Spodoptera frugiperda* insect cells in the insect cell culture medium of claim 2; and recovering the grown insect cells.

5. The insect cell culture medium of claim 1, wherein the insect culture medium further does not contain aspartate.

6. A method of culturing *Spodoptera frugiperda* insect cells, comprising the steps of:

growing the *Spodoptera frugiperda* insect cells in the insect cell culture medium of claim 5; and recovering the grown insect cells.

7. A method of culturing *Spodoptera frugiperda* insect cells, comprising the steps of:

growing the *Spodoptera frugiperda* insect cells in the insect cell culture medium of claim 1; and recovering the grown insect cells.

8. The method of claim 7, wherein the *Spodoptera frugiperda* insect cells are selected from the group consisting of *Spodoptera frugiperda* cell line Sf-9 and *Spodoptera frugiperda* cell line Sf-21.

9. An insect cell culture medium for culturing *Spodoptera frugiperda*, wherein the insect cell culture medium does not contain glutamine, glutamate, and aspartate, and wherein the insect culture medium comprises an added ammonium salt.

* * * * *